United States Patent [19]
Offray et al.

[11] Patent Number: 5,545,217
[45] Date of Patent: Aug. 13, 1996

[54] BREAST IMPLANT

[75] Inventors: Denise A. Offray, Gillette; Durmus Koch, St. Demarest; John Mortensen, Little Silver, all of N.J.

[73] Assignee: C. M. Offray & Son, Inc., Chester, N.J.

[21] Appl. No.: 425,607

[22] Filed: Apr. 20, 1995

[51] Int. Cl.⁶ .................................................. A61F 2/12
[52] U.S. Cl. .......................................................... 623/8
[58] Field of Search ............................................ 623/7, 8

[56] References Cited

U.S. PATENT DOCUMENTS

| | | |
|---|---|---|
| 3,189,921 | 6/1965 | Pangman . |
| 3,293,663 | 12/1966 | Cronin . |
| 3,654,914 | 4/1972 | Franklyn . |
| 4,485,096 | 11/1984 | Bell .................................... 424/95 |
| 4,710,162 | 12/1987 | Johnson . |
| 4,863,733 | 9/1989 | Startz . |
| 4,892,539 | 1/1990 | Koch .................................... 623/1 |
| 4,936,858 | 6/1990 | O'Keefe .................................... 623/8 |
| 4,994,084 | 2/1991 | Brennan . |
| 4,995,882 | 2/1991 | Destouet .................................... 623/8 |
| 4,995,907 | 2/1991 | Ledergerber .................................... 623/8 |
| 5,002,071 | 3/1991 | Harrell .................................... 128/897 |
| 5,171,269 | 12/1992 | Bark .................................... 623/7 |

FOREIGN PATENT DOCUMENTS 0230672  5/1987  European Pat. Off. .

*Primary Examiner*—Randy C. Shay
*Attorney, Agent, or Firm*—Reid & Priest LLP

[57] ABSTRACT

A breast prosthesis implant is disclosed comprising a generally conical bio-compatible fabric shell. The shell is pervious to tissue growth and body fluids. The interior of the shell is divided into series of discrete chambers separated by pervious fabric dividers, the chambers containing masses of bio-compatible fibers. The fiber concentration in the chambers nearest the apex of the cone is less than the concentration in chambers progressively further from the cone apex. Preferably, the shell is somewhat stretchable to permit the volume of the shell to increase or decrease in accordance with the weight gain or loss of the patient.

9 Claims, 1 Drawing Sheet

BREAST IMPLANT

BACKGROUND OF THE INVENTION

The present invention is directed to a prosthetic device and specifically to an improved compound prosthesis intended to be implanted in a female breast following removal of diseased body tissue.

Still more particularly, the invention is directed to a bio-compatible breast implant characterized in that following an initial period after implant provides the patient with a close simulation of a natural breast.

PRIOR ART

Numerous attempts have been made to provide an implantable breast prosthesis which resembles, both to the patient and to third persons, a close simulation of the normal breast.

The use of liquid silicone implants is counter indicated in view of the deleterious effects which may result from silicone leakage.

Implants comprised of silicone pouches filled with saline or the like are deficient in many respects. Specifically, since pouch must be only partially filled to avoid rupture, the weight of the liquid forms the slack pouch into visible ripples. Also, the temperature of the liquid is retained over protracted periods such that when the patient moves from a cold to a warm environment, for example, the implant will continue to feel cold. It is also possible, upon exposure to the sun, for actinic rays to penetrate the pouch and damage tissues normally protected by the healthy breast.

Attempts have been made to fabricate implants from biocompatible materials, illustratively DACRON (a trademark of the Dupont Corporation).

By way of example, U.S. Pat. No. 4,936,858 discloses a composite implant comprised of a net-like pouch of biocompatible fabric which encompasses a further pouch filled with a gel in a silicone sack. The fabric material is selected to permit substantial in-growth of body tissues, so as to fix the prosthesis at the implant site.

U.S. Pat. No. 3,293,663 discloses the use of a tissue pervious porous polyester fabric secured to the posterior surface of a silicone filled sack, the fabric functioning, upon tissue in-growth, to anchor the prosthesis.

U.S. Pat. No. 3,189,921 discloses a foam type implant having a sponge shell whose outer surface is pervious to fibrous tissue and blood, the shell having an inner surface which is pervious to body fluids but impervious of cellular structure. The reference notes that prior foam implants were undesirable in that they permitted in-growth of fibrous tissues throughout the foam resulting in an implant which hardens.

Each of the noted approaches to providing a "natural" breast implant have, for one or more reasons, failed to achieve commercial success.

SUMMARY OF THE INVENTION

The present invention may be summarized as directed to a prosthetic device intended specifically for use as a breast implant and characterized in that it presents no health hazard, is not subject to migration from the implant site, is comfortable to the patient and presents, both from an appearance and tactile standpoint, the characteristics of a natural female breast.

An important feature of the device of the invention is that to a limited degree the implant is able to increase and decrease in size in accordance with the gain or loss of weight by the patient. Since new blood vessels and tissue will develop throughout the structure of the device normal body temperature will be maintained at the structure site in contrast to known liquid-filled prosthesis which vary from body temperature when subjected to cool or hot environments.

Briefly stated, the prosthetic device of the invention is comprised of a bio-compatible structure comprised of a homopolymer polyester, illustratively fiber identified as FORTREL, polyester type 302, manufactured by WELLMAN INC.

A characterizing feature of the device of the invention is that the prosthesis is comprised of a generally conical structure preferably of deformable warp knit fabric internally sub-divided into a series of chambers by generally parallel spaced fabric dividers extending generally perpendicularly to the axis of the conical structure. The dividers which are preferably resistant to stretching form the interior of the structure into a series of chambers, the chambers each containing a fill of bio-compatible fibers.

The fibers and the fabric sub-dividing the chambers are selected such as to provide controlled permeability both to body fluids and tissue growth, the tissue growth in particular being controlled by the fiber density and to a lesser degree, the permeability of the dividers such that the degree of tissue in-growth into the various cells or chambers is greatest in the anterior chambers, tissue in-growth into progressively posteriorly related chambers being progressively less.

The structure of the device is intended to promote a relatively high degree of tissue in-growth in the lower density fiber-filled anterior chambers with progressively lower in-growth in posteriorly located more densely fiber-filled chambers.

More particularly, the fiber fill in the posterior chambers is effected to a higher density, with the respective chambers toward the anterior or nipple adjacent chamber being filled to a lower density of fiber. Both the external surface of the prosthesis and the dividers are pervious to body fluids, the external surface of the prosthesis being preferably fabricated of a velour type distensible and, to a degree, deformable knitted structure to assure rapid tissue in-growth to provide locational stability to the device promptly after implant.

It is accordingly a primary object of the invention to provide a breast prosthesis which may be permanently implanted and which replicates, as nearly as possible, the characteristics of a natural breast.

A further object of the invention is the provision of a prosthesis comprised of bio-compatible fabrics which obviates the disadvantageous aspects of prostheses heretofore known.

A further object of the invention is the provision of a breast prosthesis characterized in that the same is divided into a series of chambers of progressively increasing base size in the configuration generally of frusto-conic structures, further characterized in that the chambers are all receptive to tissue in-growth as well as pervious to body fluids, and in that posteriorly located chambers are filled with progressively denser fibrous materials and are, hence, less receptive to tissue in-growth than anteriorly related chambers thereby to provide a device which closely replicates the characteristic of a natural breast.

Still a further object of the invention is the provision of a prosthesis of the type described having an exterior surface comprised of velour like knitted material whereby to encourage the rapid in-growth of tissue into the knitted structure to promptly and permanently locate the prosthesis.

A still further object of the invention is the provision of a breast prosthesis which, to a degree, is enabled to expand and contract in accordance e.g. with the gain or loss of weight of the patient whereby the body defines the shape of the structure, rather than the structure defining the shape of the body.

A still further object of the invention is the provision of a prosthesis of the type described having a life expectancy coincident with the life of the patient, i.e. to eliminate the necessity for adjustment or replacement as is the case with implants heretofore known.

DETAILED DESCRIPTION OF DRAWINGS

Figure 1:
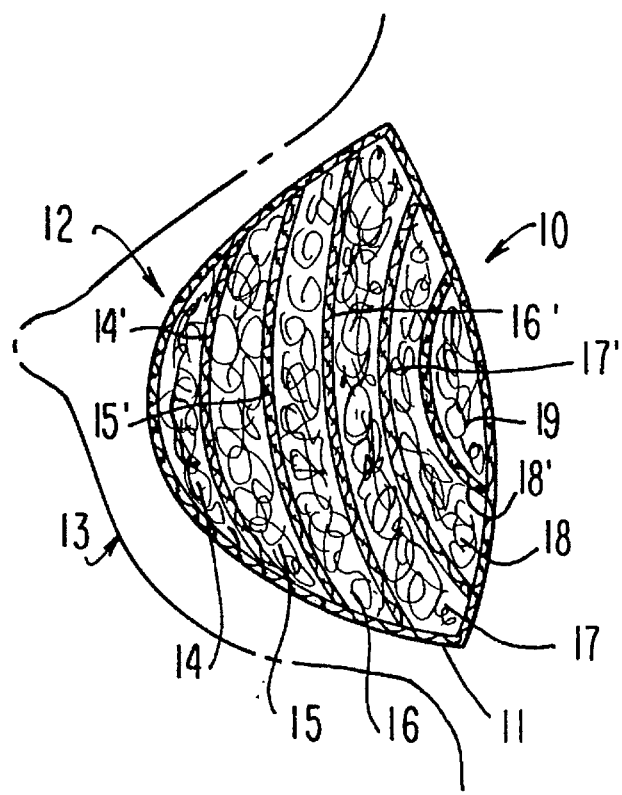
FIG. 1 is a schematic view of a prosthesis in accordance with the invention implanted within the breast.

In FIG. 1 there is disclosed an implant or prosthesis 10 in accordance with the invention. Details of the specific fibers and like materials will be described in a further section of the instant application.

Referring to FIG. 1, the prosthesis 10 is comprised of a generally conical configuration including a exterior, preferably warp knit and stretchable fabric 11, the external configuration of the anterior portion 12 being configured generally in a convex mode which conforms generally to the desired configuration of the external surface 13 of the breast. As will be obvious, the size and shape of the prosthesis will be varied in accordance with the requirements of the patient.

The interior of the prosthesis 10 is divided into a series of chambers 14, 15, 16, 17, 18 and 19 in the illustrative embodiment, it being understood that as few as two chambers may be provided and that 6 represents a probable maximum.

Chambers 14 through 19 are defined by transversely directed fabric dividers 14' through 18' the dividers being less stretchable than fabric 11. The chambers 14 through 19 contain filler fibers as more fully described hereinafter, the fiber density within the chambers increasing progressively from the anterior most chamber 14 to the posterior most chamber 19, the fibers F as depicted in FIG. 1 being schematically illustrated as disposed in parallel to illustrate the variations in concentration, it being understood that in the actual structure the fiber bundles are preferably randomly oriented.

The divider fabrics 14' through 18' are comprised of pervious material, both to body fluids and to fibrous tissue growth. The external fabric 12 is likewise pervious to fluid and tissue growth, the fabric 12 preferably including a velour like or looped external surface.

Figure 2:
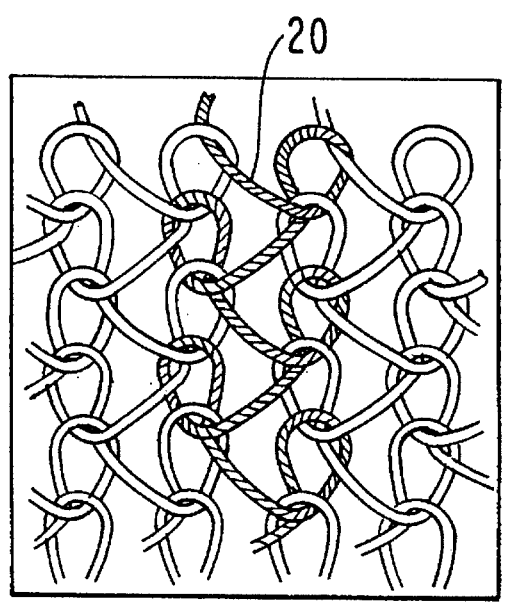
FIG. 2 is a schematic magnified plan view of a preferred tricot knit material intended to be used as the exterior component of the implant.

To this end, there is disclosed in FIG. 2 by way of representative example, a plan view of a tricot knit fabric 12 a running line of loops or stitches of the knit being stippled to emphasize the broad loops 20 defined on the outer surface of the knit as an inherent element thereof° While a tricot knit has been illustrated, satisfactory results may likewise be obtained by the use of a Raschel knit, the important characteristics of the fabric 12 being relative stretchability and the existence of velour like external loops.

While knitted-stretchable fabrics are preferred, it is feasible to employ certain woven fabrics such as those disclosed in U.S. Pat. No. 4,892,539 issuing to one of the inventors named herein, as well as U.S. Pat. No. 4,517,687, both of said patents being herein incorporated by reference.

It is to be understood that the fabrics of the cited patent references are employed herein in a totally different environment than that called for by the patents, and specifically are intended to be pervious to fluids and tissue in-growth in the instant environment, whereas in the environment described in the patents (vascular grafts) tubular increments of the fabrics are rendered impervious by infusion with the blood of the patient which is coagulated on the interior surfaces. While the woven fabric of the patent references is structurally acceptable, the woven fabrics thereof have the disadvantage of limited stretchability with the result that fold lines or creases in the prosthesis may not be avoidable.

Best Mode Disclosure

In keeping with the requirements of the Patent Laws there is described herein below the best mode currently known to applicants in respect of the characteristics of fabric and filler for the implant.

It is to be understood that the materials are described by way of example and not by way of limitation, and that it is anticipated that other materials, both known and hereafter created, would function adequately in the environment of the prosthetic device.

A preferred yarn for fabricating the exterior 12 is a homopolymer polyester with minimal additives or contaminants. Suitable fibers are manufactured by the Dupont Corporation and identified as DACRON TYPE 56T and by WELLMAN INC. under the trademark FORTREL (TYPE 302). The fibers used in the formation of the knitted shell 12 are preferably comprised of a 50 denier multi-filament textured dacron type 56, the yarn being comprised of 47 filament fibers making up the bundle.

The filaments making up the yarn of the preferred example are 1.06 denier filament diameter, successful results being anticipated with fibers in the range of 0.4 to 3 denier.

Knitting is effected to provide a fabric having a weight of 1.5 to 6 ounces per square yard, 2½ ounces per square yard being considered optimal. The knitting of the yarns within the noted weight ranges provides a liquid permeability of the resultant fabric from a minimum of about 50 cc/cmsq./min. at a standard of 120 mm of mercury pressure for the least densely woven material to approximately 10,000 cc/cmsq./min. for the minimum density material.

A preferred permeability value for the fabric 12 is approximately 2000 cc/cmsq./min. The internal layers 14' through 18' are preferably of high permeability, i.e. greater than 2000 cc/cmsq./min. The internal layers 14' through 18' are preferably, but not necessarily, woven. The use of the stretchable or distensible external fabric 12 in combination with the woven and hence more shape retaining internal dividers provides a unique structure which is enabled to expand and contract with minimal distortion in a radial direction.

The polyester polymer yarns used for the various fabrics may be textured or untextured, textured being preferred since it enhances tissue in-growth.

With respect to the fiber employed in filling chambers 14 through 19 the Wellman Type 302 is preferred. The denier of the fiber filaments may vary from anywhere between 0.4 denier to about 3.5 denier. A preferred value comprises fiber chopped into lengths of about 1½ inches with a weight of 2.25 denier. Fiber lengths may range from ½ inch to over 4 inches with shorter fibers used in the anterior located chambers.

With respect to the density of fiber fills, the fiber density will increase in the posteriorly located chambers to as much as approximately 0.36 grams per cubic centimeter of polyester staple fiber. Fiber density in the anterior most chamber may be as small as 0.01 grams per cubic centimeter. The densities noted are calculated based on the preferred 2.25 denier, 1½ inch lengths fibrous materials.

From the foregoing, it will be appreciated that there is provided in accordance with the invention a new and improved breast prosthesis which is permanent, and which, after implant, accurately replicates the natural human breast in all aspects. When constructed of the preferred somewhat stretchable fabric, due to the distensibility of the device, and the encouraged in-growth of body tissue and fluids, a degree of volumetric distention and contraction of the prosthesis as well as limited contour variation is possible to coordinate the size of the prosthesis with weight gain or loss by the patient. In contrast with known prosthesis where the size of the device controls the shape of the body, in the instant device the body controls the size of the prosthesis.

It is important to note that each of the chambers defined by the interior partitions provides an environment for the in-growth of body tissue, the amount of tissue in-growth and fluid retention being controlled in accordance with the density of fiber fill within the respective partitioned chambers. By providing chambers having different fiber densities in combination with a highly permeable retaining structure there is created for the first time a prosthetic breast implant which may be tailored to the specific requirements of the patient to enable desired cosmetic and tactile end results.

Since the interior of the prosthesis will ultimately be permeated with living tissue, the implant will be retained essentially at body temperature and the thermally induced discomfort inhering in the use of liquid filled devices avoided.

As will be apparent to those skilled in the art and familiarized with the instant disclosure numerous variations in details of construction and selection of materials may be made without departing from the spirit of the invention. Accordingly the invention is to be broadly construed within the scope the appended claims.

Having thus described the invention and illustrated its use, what is claimed as new and is desired to be secured by Letters Patent is:

1. A breast prosthesis implant comprising a bio-compatible tissue and body fluid pervious fabric shell in the general configuration of a cone, a plurality of pervious partitions extending transversely within said shell and dividing said shell into a series of chambers, and bio-compatible fibrous masses disposed within said chambers.

2. A prosthesis in accordance with claim 1 wherein the density of said fibrous masses increases progressively from the chamber closest to the apex of the cone to the chamber most remote from the apex of the cone.

3. A prosthesis in accordance with claim 1 wherein said shell includes a velour outer surface portion.

4. A prosthesis in accordance with claim 1 wherein said shell and fibrous masses are comprised of a homopolymer polyester material.

5. A prosthesis in accordance with claim 1 wherein said shell comprises a woven fabric including on the external surface thereof loops.

6. A prosthesis in accordance with claim 1 wherein said partitions are comprised of open weave fabric.

7. A prosthesis in accordance with claim 1 wherein said shell comprises a stretchable knitted fabric whereby the same may increase and decrease in volume.

8. A prosthesis in accordance with claim 7 wherein said partitions are woven fabric and are less stretchable than the fabric of said shell, whereby said prosthesis is susceptible to greater growth in the direction of the axis of said cone than in a radial direction.

9. A prosthesis in accordance with claim 8 and including at least two said partitions dividing the interior of said prosthesis into at least three said chambers, the concentration of said fibrous masses increasing progressively in the chambers more remote from the apex of said shell.

\* \* \* \* \*